United States Patent [19]

Gonser

[11] 3,987,796
[45] Oct. 26, 1976

[54] ELECTROSURGICAL DEVICE
[75] Inventor: Donald I. Gonser, Forest Park, Ohio
[73] Assignee: Dentsply Research & Development Corporation, Milford, Del.
[22] Filed: July 2, 1975
[21] Appl. No.: 592,480

Related U.S. Application Data
[62] Division of Ser. No. 461,983, April 18, 1974, Pat. No. 3,905,373.

[52] U.S. Cl. .......................... 128/303.14; 317/18 B
[51] Int. Cl.² ...................... A61B 17/36; A61N 3/02
[58] Field of Search ................. 128/303.13, 303.14, 128/303.17, 303.18, 2.1 P, 421, 422, 423; 317/18 A, 18 B, 18 D

[56] References Cited
UNITED STATES PATENTS
2,823,678  2/1958  Luftman et al. ..................... 128/422
3,601,126  8/1971  Estes .............................. 128/303.14
3,683,923  8/1972  Anderson ....................... 128/303.14
3,699,967  10/1972 Anderson ....................... 128/303.14
3,812,858  5/1974  Oringer .......................... 128/303.14

Primary Examiner—Robert W. Michell
Assistant Examiner—Lee S. Cohen
Attorney, Agent, or Firm—James W. Pearce; Roy F. Schaeperklaus; J. William Berkstresser

[57] ABSTRACT

A radiofrequency electrosurgical device which includes an active electrode and a passive electrode coupled to a chassis ground of a radiofrequency generator of the device. If the passive electrode is disconnected from the chassis ground, a potential develops between the chassis ground and a system ground. This potential is used to actuate a relay to disable the radiofrequency generator if the passive electrode becomes disconnected. The relay is reset when a main power off-on switch is turned to off position.

2 Claims, 1 Drawing Figure

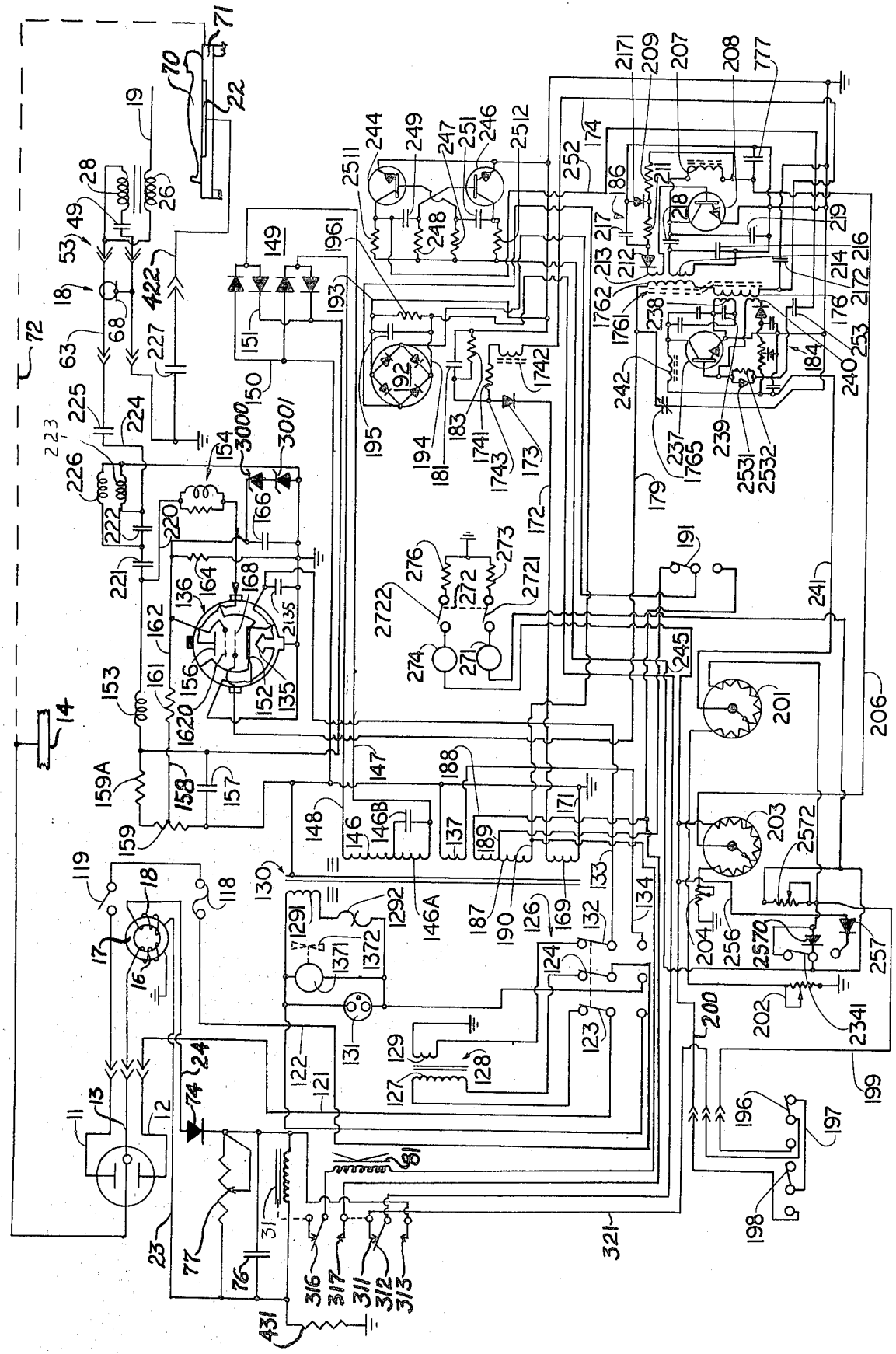

ELECTROSURGICAL DEVICE

This is a division of my co-pending application Ser. No. 461,983 filed Apr. 18, 1974, now U.S. Pat. No. 3,905,373 issued Sept. 16, 1975.

This invention relates to an electrosurgical device. The device of this invention represents an improvement in the type of device shown in my U.S. Pat. No. 3,870,047 issued Mar. 11, 1975.

In radio-frequency electrosurgical devices, a passive electrode having a broad face engaging a patient is used to link the patient to a chassis ground connection. It is essential that the connections linking the passive electrode to the chassis ground be unbroken to avoid danger to the patient by inadvertent alternate radio-frequency return paths from the patient. Such inadvertent alternate radio-frequency return paths can cause radio-frequency skin burns on the patient. Various systems have been devised to monitor the integrity of a passive electrode radio-frequency return path grounding system using direct or low frequency interrogation currents which can conduct through the patient under some circumstances. However, such currents can be dangerous to the patient, and an object of this invention is to provide a monitoring system which does not require an unsafe interrogation monitoring current which, when present, may pass through the patient.

It has been determined that, if a passive electrode is not properly linked to chassis ground in such a device, a radio-frequency potential is set up in between the chassis ground and system ground if a small inductance is placed between the system ground and the chassis ground, and a further object of this invention is to provide a monitoring system which uses this potential to signal a passive electrode ground failure.

A further object of this invention is to provide such a monitoring system which shuts off the electrosurgical device if a predetermined radio-frequency potential is set up between chassis ground and system ground.

Briefly, this invention provides a radio-frequency electrosurgical generator device which includes a transformer which has a primary winding in a line which connects system ground to chassis ground. A secondary winding of this transformer operates a relay having contacts which disconnect a power lead to a driver oscillator of the device and actuate a buzzer horn when the predetermined radio-frequency potential is set up. Other contacts of the relay actuate an electrical hold-in circuit which prevents re-energizing of the radio-frequency active output lead until the generator device has been turned off.

The above and other objects and features of the invention will be apparent to those skilled in the art to which this invention pertains from the following detailed description and the drawing which:

The drawing is a schematic circuit diagram of a radio-frequency electrosurgical device constructed in accordance with an embodiment of this invention.

In the following detailed description and the drawing, like reference characters indicate like parts.

In the drawing is shown schematically the wiring diagram of a radio-frequency electrosurgical device constructed in accordance with an embodiment of this invention. Alternating current power is supplied by power leads 11 and 12. A grounding line 13 is connected to an appropriate system ground such as a water pipe 14 and/or to an appropriate operating room grounding system. The grounding line 13 is connected to one side of a primary winding 16 of a transformer 17. The other side of the primary winding 16 is connected to a chassis ground. In the drawing, a ground symbol indicates chassis ground. When a radio-frequency potential is set up between the system ground 14 and the chassis ground, a potential is set up by a transformer secondary 18 between leads 23 and 24. A power line fuse 118 is provided in the lead 11. An interlock switch 119 is closed during operation of the device but can be arranged to open when a casing of the device (not shown) is opened.

Leads 121 and 122 are connected to poles 123 and 124, respectively, of a triple pole double throw on-off switch 126. When the on-off switch 126 is in the position shown (off position), the leads 121 and 122 are connected to power a primary winding 127 of a transformer 128 to impress a low voltage such as 4 volts on a secondary winding 129 thereof. When the on-off switch 126 is in its other position (on position), the leads 121 and 122 are connected to a primary winding 1291 of a transformer 130 to power the transformer. A panel light 131 is connected in parallel with the primary winding 1291 to indicate that the primary winding 1291 is powered. A thermally activated circuit breaker 1292 in series with the primary winding 1291 protects the transformer 130. A third pole 132 of the switch 126, when in the on position, connects leads 133 and 134 to connect one side of a heater electrode 135 of a tetrode main power amplifier tube 136 to one side of a first secondary winding 137 of the transformer 130, which can be constructed to produce approximately 6 volts AC to the heater electrode 135. A capacitor 2135 is connected between the line 133 and ground to shunt any radio-frequency current from the heater electrode 135. The other side of the first secondary winding 137 is connected to ground as is the opposite side of the heater electrode 135. A fan motor 1371 is also connected in parallel with the primary winding 1291 to drive a fan 1372 which blows air on the tetrode 136 and other components to cool the tetrode and other components. When the on-off switch 126 is swung to its off position, the pole 132 connects the lead 133 to the secondary winding 129 of the transformer 128 so that the heater electrode 135 is heated not only when the on-off switch 126 is in the on position but also when the on-off switch 126 is in the off position. As already pointed out, the secondary winding 129 of the transformer 128 can be arranged to deliver about four volts so that the heater electrode 135 is heated but at a lower temperature when the switch 126 is in the off position but is maintained at a sufficient temperature that the device will operate at once when the switch 126 is turned on.

A secondary winding 146 of the transformer 130 supplies a voltage of approximately 2000 volts AC across leads 147 and 148 to a full wave bridge rectifier 149 which supplies 2000 volts direct current across leads 150 and 151.

A secondary winding 146 of the transformer 130 supplied a voltage of approximately 2000 volts AC across leads 150 and 151. The lead 150 is connected to ground as is a cathode 152 of tetrode 136. The lead 151 is connected through a plate choke 153 and a parasitic suppressor network 154 to a plate 156 of the tetrode 136 so that 2000 volts DC is impressed between the cathode 152 and the plate 156 of the tetrode 136. A filter condenser 157 smooths out wave form ripple from the rectifier 149. A tapped resistor 159 and a fixed resistor 159A are connected in series across the leads 150 and 151. A lead 158 connected to the tap of the tapped resistor 159 supplies a positive potential through a resistor 161 and a lead 162 to a screen grid 1620 of the tetrode 136. A voltage of approximately 380 volts can be taken off at the tap which is maintained on the screen grid. An appropriate resistance 164 bleeds off screen grid current to chassis ground. A capacitor 166 connected between the screen grid lead 162 and ground removes or shunts out radio frequency from the screen grid. Zener diodes 3000 and 3001 connected in series suppress voltage transients and regulate the maximum steady state voltage on the screen grid 1620.

A section 146A of the second secondary winding 146 of the transformer 130 is connected in parallel with a capacitor 146B to form a tuned circuit tuned to a line input frequency, which can be 60 Hertz, to stabilize the secondary winding voltages to a variation of approximately ±1% with a change in input voltage of ±10% impressed on the primary winding 1291. Thus, the transformer 130 is a substantially constant voltage transformer stabilizing all the circuitry of the device.

A bias voltage for a control grid 168 of the tetrode 136 is supplied by a third secondary winding 169 of the transformer 130. A first lead 171 from the winding 169 is connected to chassis ground and a second lead 172 from the winding 169 is connected to a rectifier 173. The rectifier 173 supplies a negative potential through a resistance 1741 and an inductance 1742 to a lead 174, which is connected to one end of a first series winding 176 of a transformer 1761. The other end of the winding 176 is connected through a second series winding 1762 of the transformer 1761 to a lead 179 connected to the control grid 168 of the tetrode 136. A condenser 181 which is connected between chassis ground and a junction 1743 smooths out the wave form of the potential from the rectifier 173. A resistance 183 connected in parallel with the condenser 181 serves to discharge the condenser 181 when the device is turned off. The bias voltage can be approximately −120 volts.

Oscillator circuits 184 and 186 for the device are powered from a fourth secondary winding 187 of the transformer 130. Leads 188, 189 and 190 from the winding 187 are connected through a single pole double throw switch 191 to a full wave bridge rectifier 192 which supplies a DC voltage across leads 193 and 194. When the switch 191 is in the position shown, a voltage of approximately 16 volts is supplied across the leads 193 and 194. When the switch 191 is in its other position, a voltage of approximately 25 volts is supplied across the leads 193 and 194. A condenser 195 connected across leads 193 and 194 smooths ripple voltage. A resistance 1961 connected across the leads 193 and 194 discharges the condenser 195 when the device is turned off. The lead 193 is connected to chassis ground. The lead 194 is a main power lead and normally is connected through normally closed contacts 311 and 312 of a relay 31 and a lead 321 to the pole of a single pole double throw switch 196. When the switch 196 is in the position shown, the lead 321 is connected through a short lead 197 to the pole of a single pole double throw switch 198. The switches 196 and 198 can be foot operated switches. The switches 196 and 198 are shown in their normal positions. When the switch 196 is turned to its other position, the main power lead 194 is connected to a lead 199. When the switch 198 is turned to its other position, while the switch 196 remains in the position shown, the main power lead 194 is connected to a lead 200. If the switches 196 and 198 are both turned to their other position, the lead 194 is connected to the lead 199, and it is impossible to connect both the leads 199 and 200 to the lead 194 at the same time. The lead 199 is connected to one side of a potentiometer 201. The other side of the potentiometer 201 is connected to chassis ground through an adjustable resistor 202. In a similar manner, the lead 200 is connected to one side of a potentiometer 203. The other side of the potentiometer 203 is connected to chassis ground through an adjustable resistor 204. Thus, when the switch 196 is advanced to its other position, a selected DC voltage is impressed across the potentiometer 201 and when the switch 198 is advanced to its other position while the switch 196 remains in the position shown, a selected DC voltage is impressed across the potentiometer 203.

A voltage between zero and the selected voltage is impressed upon a lead 206 connected to the tap of the potentiometer 203 when the switch 198 is in its other position and the switch 196 is in the position shown. The lead 206 is connected through an inductance or choke 207 to the collector of a transistor 208, which is a part of the oscillator circuit 186. The emitter of the transistor 208 is connected to chassis ground. The lead 206 is also connected through resistors 209 and 211 and a rectifier 212 to one side of a tickler coil 213. The rectifier 212 functions to reverse bias the base of the transistor 208 and is connected to one side of the tickler coil 213, which is excited by a tank circuit consisting of an inductance 214 and a condenser 216 coupled to the transistor 208 in which continuous oscillation is set up by the tank circuit. The other side of the tickler coil 213 is connected to the base of the transistor 208. The rectifier 212 establishes the reverse bias required by the base of the transistor 208 and is also connected to chassis ground through a condenser 217 which establishes the bias network circuitry. A bias rectifier 2171 is connected between chassis ground and a junction between the resistors 209 and 211. The tank circuit is connected with the collector of the transistor 208 through a coupling condenser 218. A condenser 219 is connected between the emitter and the collector of the transistor 208 to shunt out radio frequency potentials. A capacitor 777 acts to provide a bypass to ground shunt for attenuating radio frequency feedback into the line 206 when the oscillating circuit 186 is in operation. The tank circuit can be tuned to oscillate at a rate of approximately 1.8 megaHertz. The oscillation is picked up by the transformer winding 1762 and the voltage thereof is multiplied by the transformer winding and impressed by way of the lead 179 on the control grid 168 of the tetrode 136 to provide an amplified output by the tetrode 136 of that frequency. The output of the tetrode 136 is impressed by way of a lead 220 on an output circuit which is coupled through condenser 221 to a tuned pie network which includes condensers 222 and 225 and inductances 223 and 226. Right-hand ends of the inductances 223 and 226 are connected to chassis ground so that, if there should be failure of the condensers 221 and 222, the direct current output of the tetrode 136 would be drained off to chassis ground without danger to the patient. A take-off lead 224 which is connected between the condenser 222 and the inductance 223 extends to one side of the condenser 225. The other side of the condenser 225 is connected to a central lead 63 of a coaxial cable 18 and through a cable end assembly 53 to one end of a driver coil 28. The other end of the driver coil 28 is connected through a condenser 49 to chassis ground. An annular conductor 68 of the coaxial cable 18 is connected to chassis ground. A passive electrode 22 is connected by a lead 422 to one side of a condenser 227. The other side of the condenser 227 is connected to chassis ground. Thus, a continuous radio-frequency oscillating potential is set up in a driver coil 26 and in an electrode 19 and an electrosurgical operation can be performed when the electrode 19 is advanced to a patient 70 mounted on a treatment table 71 with the passive electrode 22 engaging the patient.

As long as the passive electrode 22 is coupled to chassis ground through the lead 422 and the condenser 227, a return path is provided for radio-frequency current, and, when the electrode 19 is brought close to or into engagement with the patient 70, an electrosurgical operation can be performed safely. However, if this coupling is broken as by electrical failure of the lead 422, the low impedance return path to chassis ground through the passive electrode is broken. As indicated by the dashed line 72, the surgical table can be at system ground, and other items which can be connected to the patient can be at system ground providing unwanted alternate return paths to system ground. A radio-frequency potential is developed between the system ground 14 and the chassis ground causing a radio-frequency potential to be set up in the transformer 17 between the leads 23 and 24. This potential is rectified by a rectifier 74 to provide a direct current potential across the coil of the relay 31 to energize the relay 31. A condenser 76 mounted in parallel with the relay coil 31 smooths out the current to the relay coil 31. An adjustable resistor 77, which is connected in parallel with the relay coil 31, can be adjusted to determine the voltage at which the relay 31 is energized. When the relay 31 is energized, normally closed contacts 311 and 312 open and normally open contacts 312-313 close to disconnect the main low voltage direct current power lead 194 from the lead 321 to de-energize the switch 196 and to connect the main low voltage direct current power lead 194 to the coil of the relay 31 to maintain the relay 31 energized through a resistor 431 to chassis ground. At the same time, normally open relay contacts 316–317 close to connect a buzzer horn 81 across the transformer leads 188 and 190 to cause the horn 81 to sound. The relay 31 is reset automatically when the main on-off switch 126 is turned to the off position.

When the on-off switch 126 is in its other or on position, the switch 198 is moved to its other position and the switch 196 remains in the position shown and a single pole double throw blend switch 2341 is in the off position shown, a continuous oscillation is impressed on the driver coil 28. When the switch 196 is moved to its other position and while the single pole double throw blend switch 2341 is in the off position shown, the oscillating circuit 184 is energized to produce an interrupted oscillation in the driver coil 28. The oscillating circuit 184 is generally similar to the circuit 186 already described and includes a transistor 237, a tank circuit inductance 238, a tank circuit capacitor 239, and a tickler coil 240 and associated elements. A lead 241, which is connected to the tap of the potentiometer 201, is connected through a choke 242 to the collector of the transistor 237. Moving of the switch 196 to its other position impresses a selected DC voltage across the potentiometer 201 and a DC voltage between zero and the selected voltage is impressed upon the lead 241. The emitter of the transistor 237 is connected to chassis ground. The oscillating circuit 184 is set in operation to deliver an oscillator frequency of approximately 1.8 megaHertz on the control grid of the tetrode 136. The lead 199, which is connected to the high side of the potentiometer 201, is also connected through the pole of the blend switch 2341 to a lead 245, which is connected to base leads of transistors 244 and 246, which form a multivibrator circuit, through resistors 247 and 248, respectively. The collector lead of the transistor 244 is coupled through a condenser 249 to the base of the transistor 246 and the collector of the transistor 246 is coupled through a condenser 251 to the base of the transistor 244. The collectors of the transistors 244 and 246 are connected to the lead 245 through resistors 2511 and 2512, respectively. Emitters of the transistors 244 and 246 are connected to chassis ground. The multivibrator circuit can be arranged to oscillate at a rate of approximately 7000 Hertz. A lead 252 from the collector of the transistor 244 is connected through a coupling condenser 253 and a rectifier 2531, and a resistor 2532 connected in parallel with the rectifier 2531, to the base of the transistor 237 so that the operation of the oscillating circuit 184 is interrupted at a rate of 7000 Hertz to put an interrupted oscillating potential on the control grid of the tetrode 136 and to supply an interrupted radio-frequency oscillating potential at the electrode 19. The rectifier 2531 and the resistor 2532 connected in parallel with the rectifier 2531 forms a network which preserves the wave form generated by the multivibrator circuit as it is transmitted to the oscillator circuit 184.

An adjustable capacitor 1765 is connected between the lead 179 and chassis ground and can be adjusted so that it tunes with the transformer secondary coils 176 and 1762 and with the capacitor 2172 so that the grid input is tuned with the plate series tuned circuit 222, 223, 225, and 226. Both of these circuits are tuned with the driver input oscillating circuits 184 and 186 at approximately 1.8 megaHertz.

When the blend switch 2341 is disposed in its other or "on" position, moving of the switch 198 to its other position while the switch 196 is in the position shown energizes both of the oscillating circuits 184 and 186. The oscillating circuit 186 is energized in the same manner as already described. The lead 200, which is connected to the switch 198, is connected through a lead 256, a rectifier 257, the blend switch 2341, the lead 245, and an adjustable resistor 2572 to the lead 199, which is connected to the right hand end of the potentiometer 201. The rectifier 257 prevents unwanted cross feed between the leads 199 and 200. A rectifier 2570 provides full direct current voltage to the multivibrator circuit associated with the transistors 244 and 246 when the direct current voltage dropping resistor 2572 is switched into the circuit, blend position, to maintain a constant voltage on the multivibrator circuit to insure stable operation. Both the oscillating circuit 184 and the oscillating circuit 186 are set in operation and an output is provided from the tetrode 136 for energizing the electrode 19 which combines the interrupted oscillation of the circuit 184 with the uninterrupted oscillation of the circuit 186.

The lead 245 of the multivibrator circuit is also connected to a sonic signalling device 271, which is constructed to produce a sound signal of a selected frequency, which can be 2900 Hz. The sonic signalling device 271 is connected to chassis ground through a pole 2721 of an on-off switch 272 and a resistor 273. Similarly, the lead 200, which is connected to the high side of the potentiometer 203, is also connected to a second sonic signalling device 274, which is constructed to produce a sound signal of a second selected frequency, which can be 4500 Hz. The sonic signalling device 274 is connected to ground through a pole 2722 of the on-off switch 272 and a resistor 276. The sonic signalling device 271 sounds when the potentiometer 201 is energized to energize the oscillating circuit 184 to produce a sound signal which indicates to the user of the device that the oscillating circuit 184 is operating. The sonic signalling device 274 similarly produces a sound signal when the oscillating circuit 186 is energized to indicate that the oscillating circuit 186 is operating. When both the oscillating circuits 184 and 186 are operating, i.e., when a blended current is being produced, a sound signal is produced which is a blend of the selected frequencies. The rectifier 2570 insures a direct current voltage on the sonic signalling device 271 when the swithc 2341 is in the blend (other or "on") position. If the user does not want sound signals, the on-off switch 272 can be opened. The resistance values of the resistors 273 and 276 determines the loudness of the sound signals.

The condenser 227, through which the passive electrode 22 is coupled to chassis ground, permits passage of radiofrequency current to permit electrosurgical action but limits passage of lower frequency current which might shock the patient. The condenser 49, through which the driver coil 28 is coupled to chassis ground, similarly permits passage of radiofrequency current but prevents passage of lower frequency current generated as a sub-harmonic of the radiofrequency current to isolate the coils 28 and 26 from such lower frequency current to eliminate the so-called "faradic" effect or involuntary muscle contraction effect.

The electrosurgical device described above and illustrated in the drawings is subject to structural modification without departing from the spirit and scope of the appended claims.

Having described my invention, what I claim as new and desire to secure by letters patent is:

1. In combination with a radio-frequency electrosurgical device, a radio-frequency generator means for powering the radio-frequency electrosurgical device and having a main power off-on switch means and a patient monitor means for detecting an abnormal operation, control means connected to the patient monitor means, the control means having a set position in which the control means provides connection between the main power off-on switch means and the radio-frequency generator means for powering the radio-frequency generator means when the main power off-on switch means is in the on position and an unset position, means connected to the patient monitor means for advancing the control means to the unset position in the event of an abnormal operation, means for resetting the control means when the main power off-on switch means is turned to the off position, and an electrical hold-in circuit means for the electrosurgical device for requiring that the main power off-on switch means be turned to the off position to reset the control means for normal operation.

2. A radio-frequency electrosurgical device which includes a radio-frequency generator, power source means for supplying power to the radio-frequency generator, a main power off-on switch means for connecting the power supply means to the radio-frequency generator, circuit means connected to the radio-frequency generator for performing electrosurgery on a patient, a patient monitoring circuit means for detecting an abnormal operation, control means connected to the patient monitoring circuit means, the control means having a set position in which the control means provides a connection between the main power off-on switch means and the radio-frequency generator for powering the radio-frequency generator when the main power off-on switch means is in the on position and an unset position in which the control means disables the power source means from powering the radio-frequency generator, means connected to the patient monitoring circuit means for advancing the control means to the unset position for disabling the power source means from powering the radio-frequency generator in the event of an abnormal operation, means for resetting the control means when the main power on-off switch means is turned to the off position, and an electrical hold-in circuit means for requiring that the main power off-on switch means be turned to the off position to reset the control means for normal operation.

* * * * *